United States Patent [19]

Stahl

[11] Patent Number: 4,842,713
[45] Date of Patent: Jun. 27, 1989

[54] POLAROGRAPHIC OXYGEN SENSOR, PARTICULARLY FOR COMBUSTION EXHAUST GASES

[75] Inventor: Roland Stahl, Freiberg, Fed. Rep. of Germany

[73] Assignee: Robert Bosch GmbH, Stuttgart, Fed. Rep. of Germany

[21] Appl. No.: 119,218

[22] Filed: Nov. 3, 1987

Related U.S. Application Data

[63] Continuation of Ser. No. 865,959, May 20, 1986, abandoned, which is a continuation of Ser. No. 692,382, Jan. 17, 1985, abandoned.

[30] Foreign Application Priority Data

Feb. 14, 1984 [DE] Fed. Rep. of Germany ..... 34051627

[51] Int. Cl.⁴ .............................. G01N 27/46
[52] U.S. Cl. .................... 204/428; 204/424; 204/425; 204/427
[58] Field of Search ................. 204/15, 421–429

[56] References Cited

U.S. PATENT DOCUMENTS

| | | | |
|---|---|---|---|
| 2,913,386 | 11/1959 | Clark | 204/415 |
| 3,978,006 | 8/1976 | Topp et al. | 204/429 |
| 4,040,930 | 8/1977 | Dillon | 204/429 |
| 4,063,897 | 12/1977 | Aoki | 204/428 |
| 4,132,615 | 1/1979 | Linder et al. | 204/428 |
| 4,140,611 | 2/1979 | Yaegashi et al. | 204/428 |
| 4,240,890 | 12/1980 | Watanabe | 204/428 |
| 4,272,349 | 6/1981 | Furutani et al. | 204/1 S |
| 4,277,322 | 7/1981 | Kane | 204/427 |
| 4,283,261 | 8/1981 | Maurer et al. | 204/428 |
| 4,292,156 | 9/1981 | Matsumoto et al. | 204/192.34 |
| 4,292,158 | 9/1981 | Muller | 204/426 |
| 4,324,632 | 4/1982 | Tantram et al. | 204/415 |
| 4,339,320 | 7/1982 | Friese et al. | |
| 4,356,065 | 10/1982 | Dietz | 204/429 |
| 4,383,906 | 8/1976 | Sano et al. | 204/424 |
| 4,502,939 | 3/1985 | Holfelder et al. | 204/426 |

FOREIGN PATENT DOCUMENTS 071971 2/1983 European Pat. Off. .
2942494 4/1981 Fed. Rep. of Germany .

OTHER PUBLICATIONS

EPO Official Action Apr. 19, 1988 and allowed main claim, in EP84 116232.

Primary Examiner—T. Tung
Attorney, Agent, or Firm—Frishauf, Holtz, Goodman & Woodward

[57] ABSTRACT

To accurately control access of measuring gas into the measuring electrode (15) of a polarographic sensor having a tubular body (12) of solid electrolyte material, the tubular body is enclosed within a protective sleeve (38) closed at one end and embodying a diffusion resistance element, or diffusion resistance zone (43/1, 43/2); if the sleeve is of metal, a separate diffusion resistance element, for example, made of aluminum oxide or spinell may be used; if the sleeve is made of ceramic, the end portion may be thickened and the diffusion resistance zone formed therein, for example, by micropores or microchannels or microducts extending therethrough.

19 Claims, 1 Drawing Sheet

POLAROGRAPHIC OXYGEN SENSOR, PARTICULARLY FOR COMBUSTION EXHAUST GASES

This is a continuation of Ser. No. 865,959, filed May 20, 1986, which is in turn a continuation of Ser. No. 692,382, filed Jan. 17, 1985, both now abandoned.

Reference to related patents, the disclosure of which is hereby incorporated by reference, assigned to the assignee of the present application.

U.S. Pat. No. 4,356,065, Dietz, Oct. 26, 1982.
U.S. Pat. No. 4,292,158, Muller et al.

Reference to related publications and patents:

German Utility Model GM 81 01 584, corresponding to U.S. application Ser. No. 326,504, Weil, filed Feb. 12, 1981, now abandoned.

German patent disclosure DE-OS 29 42 494.

U.S. Pat. No. 4,324,632 Tantram et al., (to which British Pat. No. 2,049,952 corresponds).

The present invention relates to an oxygen sensor and more particularly to an oxygen sensor of the polarographic type. The principle of polarographic oxygen sensing is described, for example, in the referenced U.S. Pat. No. 4,356,065, Dietz, Oct. 26, 1982. The sensor in accordance with the present invention is suitable for sensing the oxygen content in exhaust gases from combustion processes, for example, from furnaces, and also combustion processes in internal combustion engines.

BACKGROUND

Oxygen sensors have previously been described, for example, in German patent disclosure document DE-OS 29 42 494 in which a solid electrolyte tube is used which has a closed bottom wall at the measuring end of the tube. The surface of the solid electrolyte tube has a counterelectrode at the inside thereof, in layer form. The outer surface of the solid electrolyte tube has a measuring electrode which is porous, and gas permeable. The measuring electrode is entirely covered with a solid porous layer which has a predetermined diffusion resistance for oxygen molecules. Such a diffusion resistance layer may be made of aluminum oxide or magnesium spinel—see, also, the referenced U.S. Pat. No. 4,356,065, Dietz. The measuring electrode and the counterelectrode have a direct voltage applied thereto, in the order of about 1 volt. The measuring portion of the solid electrolyte tube can be heated by an electrical resistance heater.

Manufacturing the diffusion resistance layer, that is, the resistance layer for the oxygen molecules, is complex and a high-precision process; the porous layer must have precisely defined characteristics, requiring highly precise and low tolerance manufacturing steps so that the pores of the diffusion resistance porous layer will be neither too small, nor too large, thus interfering, on the one hand, with diffusion of oxygen molecules or permitting excess oxygen molecules to reach the measuring electrode. The basic concept consists in limiting the quantity of the oxygen which reaches the electrode to such values that, after the electrodes have a voltage thereacross, an oxygen molecule which migrates to, and reaches, the measuring electrode is immediately converted by electrode reaction. The current which will flow between the electrodes of the sensor will have a value determined solely by the amount of oxygen molecules reaching the electrode after diffusion.

The German disclosure document DE-OS 29 42 494 also describes the heater structure. In accordance with this disclosure, the heater structure is secured to a protective tube, or integrated therewith, surrounding the solid electrolyte tube. It has also been proposed to provide a heater for the solid electrolyte tube by locating the heater in the form of a heater rod extending within the interior of the hollow solid electrolyte tube—see, for example, the referenced German utility model publication No. 81 01,584.

U.S. Pat. No. 4,292,158, Muller et al. assigned to the assignee of the present application, describes manufacture of the diffusion resistance portion or element in form of gas permeable channels or ducts rather than in form of a porous coating. This is a suitable arrangement—although, also, requiring high precision manufacturing technology.

THE INVENTION

It is an object to provide an oxygen sensor which can be made under mass production conditions not requiring high precision technology in the manufacture of the sensor itself.

Briefly, a closed solid electrolyte tube is used, surrounded externally by a protective tube, which is sealingly secured to the metal housing. The spacing between the tube and the sensing electrode on the solid electrolyte body is maintained as small as possible, in order to avoid an undesired long response speed of the sensor, for example, when installed in the exhaust system of an automotive vehicle. The "dead space" adjacent to the electrode is a minimum. In order to insure access of the measured or test gas to the sensing electrode under controlled conditions, that is, to permit passage of oxygen molecules only under controlled conditions, the protective tube is formed with a region which is gas-permeable under controlled conditions, so that only the requisite and desired number of oxygen molecules can pass through the opening. In other words, the quantity of gas, and hence the oxygen therein, diffused towards the sensor electrode itself is throttled or reduced to such an extent that migration conditions will occur which are comparable to measuring oxygen concentraation in liquids in which the diffusion speed is reduced by a factor of about $10^5$. The migration of oxygen molecules is sufficiently throttled to control the speed of the consequent reaction and, hence, the value of the current which flows. Only under such conditions will the sensor operate under diffusion-limited-current conditions, which are analog-dependent on oxygen concentration. In accordance with a feature of the invention, a separate diffusion resistance element, that is, a diffusion resistance element which permits passage of oxygen molecules, is inserted in the protective tube. This diffusion resistance element can be made before assembling and making the entire structure, so that the overall manufacturing costs of making the entire structure is substantially reduced since the manufacturing steps are simplified.

The oxygen sensor may be so constructed that, for example, when high response speed is not needed, as is the case, for example, in furnace and boiler installations, the diffusion resistance element can be made as a separate structure, without risk of a reject structure being applied to the expensive solid electrolyte tube and the layer electrodes thereon, which are frequently made of platinum, or a platinum-type metal. The solid electrolyte tube can be constructed separately from the diffusion resistance element, and the diffusion resistance element can then be matched to the remainder of the sensor structure with the proper diffusion resistance, in modular construction. For automotive applications, and when a more rapid response is required, the spacings can be so arranged that the response is sufficiently fast—considering the inherent inertia in an automotive engine—to still provide use of the sensor in automotive control systems controlling the composition of the exhaust gases from an automotive internal combustion engine.

DRAWINGS

DETAILED DESCRIPTION

Figure 1:
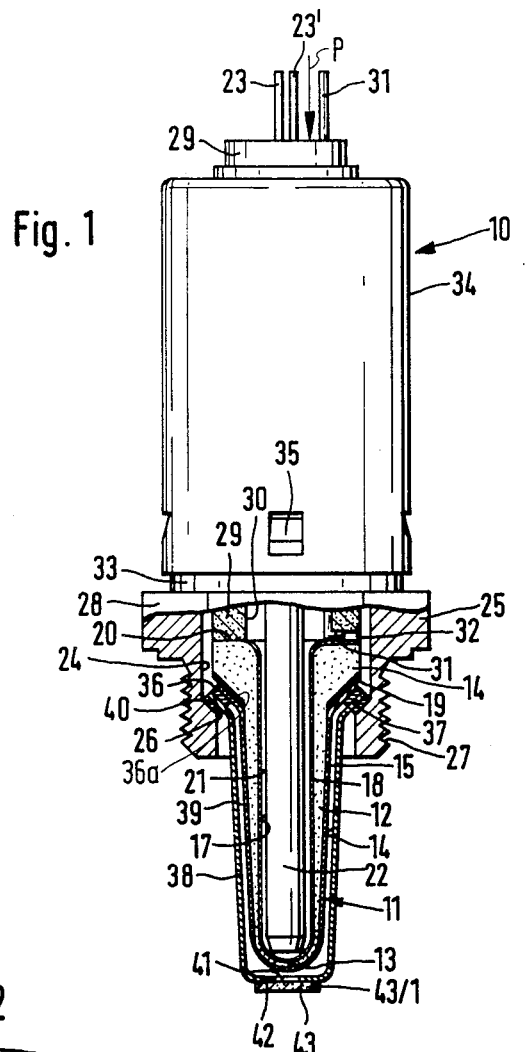
FIG. 1 is a longitudinal cross sectional view through a sensor in accordance with the present invention, in which elements which are conventional are shown only in schematic or side view form, and illustrating, in detail, only the features necessary for an understanding of the present invention; the measuring end portion is enlarged with respect to the actual size.

FIG. 1 illustrates the general construction of an oxygen sensor 10 having a sensing element 11 which is designed to operate according to the polarographic principle. This sensing element 11 has a solid electrolyte body 12, formed as a closed tube, and made of a material which is oxygen ion conductive. At the measuring end portion, the tube 12 is closed by a bottom 13; at the remote, and open end, a flange 14 is provided. The solid electrolyte tube 12 is made of stabilized zironium dioxide and has a layer 15 at its outer surface 14. The layer 15 forms a gas permeable measuring electrode. A counterelectrode 18 is located at the inside surface 17, likewise in layer form, and covering at least a portion of the surface 17. The measuring or sensing electrode 15, which, for example, may be made of platinum, terminates at its remote, or connecting end portion adjacent the flange 14 in a shoulder 19 of the flange 14 and, in this region, preferably is separated by a gas sealing, or impervious insulating layer 36a as is known. The counterelectrode 18, likewise a platinum layer for example, reaches down to the bottom 13 of the solid electrolyte tube 12 and terminates at the facing surface 20 of the connecting or inner end portion of the solid electrolyte tube 12.

The construction so far described is similar to that also shown in the referenced German patent disclosure document DE-OS 29 42 494.

In a preferred embodiment, the interior space 21 of the solid electrolyte tube 12 has a heater element placed therein, shown as a rod-formed resistance heater 22 which extends down to about the bottom 13 of the solid electrolyte tube 12 and is so positioned that its outer circumference is close to, but electrically insulated from, the inner surface 17 of the electrolyte tube 12. The rod-formed resistance heater 22 has connecting wires 23,23' which extend from the connecting portion of the sensor 10. This heater construction, also, is known and has been described, for example, in German utility model DE-GM 81 01,584.

The connecting end portion of the solid electrolyte tube 12, including the flange, 14 is located in the longitudinal bore 24 of a metal housing, for example of steel, 25. The longitudinal bore 24 of the metal housing 25 is formed with a shoulder 26 opening towards the connecting portion. The oxygen sensor 10 can be inserted into a tube or pipe, for example the exhaust manifold from an automotive engine, or an exhaust or flue pipe from a burner, furnace or the like by screwing the sensor with thread 27 into a suitably tapped hole of the metal pipe or manifold; a hexagonal gripping surface, similar to the nut-gripping surface on a sparkplug 28, is provided to tighten the metal housing into such a metal pipe or manifold. Sealing elements to seal the sensor into a pipe or manifold, as they are well-known, have been omitted from the drawing for clarity and may be constructed in accordance with any well known arrangement.

The longitudinal bore 24 of the metal housing includes a ceramic support element 29, which engages the solid electrolyte tube 12 adjacent its end face 20. The support element 29 has a longitudinal bore 30 through which a portion of the rod-like resistance heater 22 extends. A connecting wire 31 likewise is located in the longitudinal bore 30 of the element 29, extending from the sensor 10 at the connecting end portion. The end portion of the wire 31 which extends towards the sensing end of the sensor is angled off and is in tight electrical engagement with end portion of the counterelectrode 18, extending over the end surface 20 of the solid electrolyte tube 12—see FIG. 1. The bent-over end portion of the connecting wire 31 is located in position in a radially extending groove 32 of the ceramic support element 29 so that it cannot shift or move, for example, if the sensor is subjected to shock or vibration, which may be the case when installed in an automotive engine. A cup spring, not shown and which may be of any standard suitable construction, presses the ceramic element 29 against the end surface 20 of the solid electrolyte tube 12. The cup spring may be located, for example, adjacent the terminal end of the sensor, and engage a shoulder formed on the element 29 and an outer metal housing 34 crimped in position on the metal sleeve-like body 25. The body 25 has a stub-like extension 33 on which the metal sleeve 34, in the form of a protective sleeve or tube is secured, and held in position by a plurality of snap-in flaps 35, engaging, for example, an internal ring or groove on the stub 33.

The shoulder 19 of the solid electrolyte tube 12 facing the measuring end of the tube is seated on a first contacting and sealing ring 36 such that the end portion of the measuring electrode 15 is clamped between the first contact and sealing ring 36 and the flange 14, without, however, extending therefrom. The first contact and sealing ring 36 may be made, for example, of a highly electrically conductive, but soft and deformable metal. Copper, or soft steel are particularly suitable. The surface facing the measuring end portion of the contacting and sealing ring 36 engages a flange 37 of a protective tube 38 at the inner end portion thereof. The protective tube 38 extends from the metal housing 25 towards the measuring end portion of the sensor, and surrounds the projecting end portion of the solid electrolyte tube 12. The protective tube 38 is so located that the spacing between the solid electrolyte tube 12, and specifically the measuring electrode layer thereon from the inner surface of the tube 38 is as small as possible, in order to have a relatively short response speed, the space permitting access of the measuring electrode 15 to gas which enters the space between the protective tube 38 and the solid electrolyte body 12 and the sensing electrode 15 thereon.

A second contacting and sealing ring 40 is located on the side of the flange 37 of the protective tube facing the measuring end portion, and the shoulder 26 of the longitudinal bore 24 of the metal housing. Sealing ring 40, suitably, is made of the same material as the first contacting and sealing ring 36 and is provided to insure that no sensing or test gas at the outside of the solid electrolyte tube can reach the counterelectrode 18 located at the inside of the solid electrolyte tube. Due to the spring element—previously referred to and not shown, and providing a bias force on the ceramic body 29 illustrated schematically only by the arrow P, the ceramic body 29 will be pressed downwardly, exerting further pressure on the flange 14 of the solid electrolyte body 12 and hence compressing the first contacting and sealing ring 36, the flange 37 of the protective tube 38 and the second contacting and sealing ring 40 and hence the shoulder 26 of the longitudinal bore of the metal housing 25 together, and thereby providing a seal with respect to gases at the outside of the solid electrolyte body with respect to the inside thereof.

The solid electrolyte body 12 has its measuring electrode layer 15 electrically connected to the metal housing 35 via the flange 37 of the protective tube 38, the second contacting and sealing ring 40 and the first contacting and sealing ring 36. The metal housing 35, thus, forms simultaneously an electrical terminal for operation of the sensor 10. An electrical voltage source, for example of about 1 volt and preferably in the range of about ½ to 1½ volts, necessary to provide electrical bias to operate the sensor 10, is connected between the connecting line 31 and ground or chassis, represented by the metal connection of the metal housing 25 via its screw thread, and connected with a sensing electrode as described. The terminal 31 is connected to the counterelectrode 18 within the inside of the solid electrolyte body by the electrical connection of the end portion of the wire with the layer 18.

The terminals 25, 31 are connected to an evaluation circuit 5 which provides the bias voltage, shown schematically by the battery 6, and the current measuring instrument, shown schematically by the ammeter 7.

Various changes and modifications may be made in the sensor construction described so far.

In accordance with the present invention, the protective tube 38 is essentially solid throughout its length except for an opening 41 which, in a preferred arrangement, is located at the measuring end portion 42 of the protective tube 38. The opening 41, in accordance with the feature of the invention, is closed off by a plate element 43, forming a carrier for a diffusion resistance element 43/1. The diffusion resistance element 43/1 is sealed in the protective tube, for example by forming part, or all of the carrier element 43, so that access of measured gas to the measuring electrode 15 on the solid electrolyte tube 12 is accurately controlled. The diffusion resistance element 43/1 includes gas permeable pores. The carrier 43 may be made of ceramic or sintered metal and can be secured to the end portion of the protective tube 38 by soldering, bonding, adhesion, cementing, or in any other suitable way so that it is connected and securely retained on the protective tube 38 while being sealed thereon. The carrier 43 preferably is secured at the outer side of the protective tube 38; it may, however, also be located at the inside of the protective tube 38.

The size of the pores of the diffusion resistance element 43/1 will depend on the use to which the sensor is to be put. If the volume portion of oxygen within sensing gas to which the sensor is exposed is to be measured, then the diffusion resistance element 43/1 should have pore diameters somewhat larger than 10 micrometers. If the concentration of oxygen in the measuring gas is to be sensed, then the distribution of pores in the diffusion and resistance element 43/1 should be arranged in accordance with the Knudsen-diffusion. The pores should be so small that practically no convection of gas will occur. Details of such structures are known, and described, for example, in the referenced Tantram U.S. Pat. No. 4,324,632.

The carrier plate 43, preferably, is located in the facing end region 42 of the protective tube 38; it may, however, also be located elsewhere, for example, in the cylindrical region of the protective tube 38 and, then, may be of essentially sleeve-like or at least part-cylindrical or part-circular construction.

Figure 2:
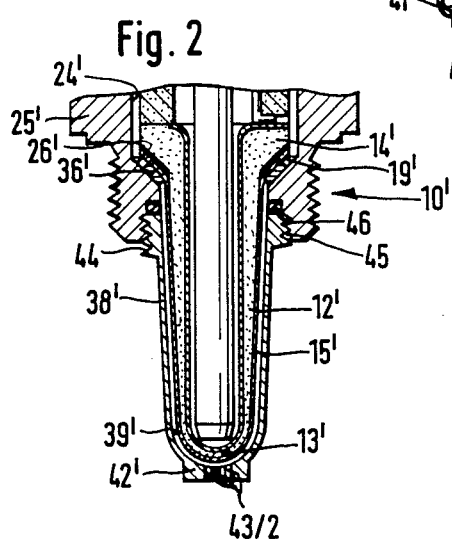
FIG. 2 is a view similar to the measuring end portion of FIG. 1, showing schematically the polarographic biasing and evaluation means and illustrating another embodiment of the invention.

Embodiment of FIG. 2: the sensor of FIG. 2 is shown only in fragmentary representation and elements similar to those shown and described in connection with FIG. 1 have been given the same reference numerals with a prime notation and will not be explained in detail.

The basic difference between the sensor of FIG. 2 and that of FIG. 1 is in the construction and arrangement of the attachment of the protective tube 38' with its diffusion resistance element 43/2. In FIG. 1, the metallic tube 38 has a flange 37 which is clamped between the sealing rings 36,40 and thus takes on the electrical function of a ground or chassis terminal for the sensor. In FIG. 2, the protective tube 38' of the oxygen sensor 10' is made of a ceramic material, for example, aluminum oxide, and has an outer thread 44 formed thereon at its side remote from the measuring end portion of the sensor. The outer thread 44 engages the inner thread 45 of a ring or flange portion 46 on which the outer thread 44 is formed. The end portion 46, thus, can be screwed into a tapped thread 45 formed in the end portion of the longitudinal bore 24' of the metal housing 25'. A sealing ring is interposed between the thickened end 46 and an inner shoulder adjacent the tapped thread 45 to provide a tight seal. In this construction, only a single contacting and sealing ring 36' is needed to ensure connection of the electrode layer 15' on the shoulder 19' on the flange 14' on the solid electrolyte tube 12', for engagement with the shoulder 26' and the longitudinal bore 24' of the metal housing 25'.

In accordance with a feature of the invention, the ceramic protective tube 38 has a measuring end portion 42' which is so constructed, that the space 39' between the bottom 13' of the solid electrolyte tube 12' and the protective tube 38' is especially small; the end portion 42' is thicker than the remainder of the tube, that is, it is reinforced. The exceedingly small space 39' increases the response speed of the oxygen sensor 10' (FIG. 2) in relation to that of the oxygen sensor 10 (FIG. 1). The reinforced end portion 42' also permit direct application of the diffusion resistance element 43/2 in the protective tube 38'. The diffusion resistance element 43/2 can be formed as a porous region within the end portion 42' of the tube 38'. In accordance with another feature of the invention, a suitably dimensioned duct or channel or passage (not shown in FIG. 2) or a plurality of such ducts or passages may be used to form diffucsion barriers for oxygen molecules.

The way the protective tube 38,38′, respectively, is connected to the sensor, and specifically to the metallic housing 25,25′ is merely illustrative; various changes and modifications may be made, the present invention being directed essentially to the way the diffusion resistance 43/1,43/2 and the carrier 43, are provided and is associated with the sensor, and specifically with respect to the solid electrolyte tube 12,12′ and the measuring electrode 15,15′ thereon.

Figure 3:
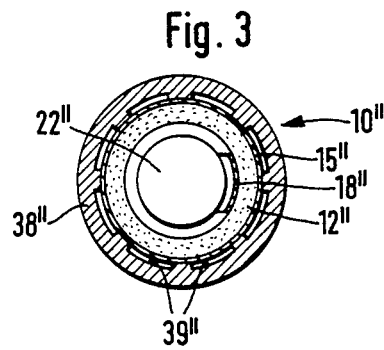
FIG. 3 is a cross sectional view through the measuring end portion of the sensor, and illustrating yet another embodiment.

FIG. 3 illustrates a cross section through an oxygen sensor 10″ showing, in cross section, the rod-like resistance heater 22″, the solid electrolyte tube 12″, the measuring electrode 15″ and the counter electrode 18″. The protective tube 38″ of the oxygen sensor 10″ has its inside engaged directly on the measuring electrode 15″; the space 39″ between the protective tube 38″ and the solid electrolyte layer 15″ is formed by grooves, striations, or, possibly even by a merely roughened surface having tiny roughness projections, preferably, for example, on the protective tube 38″. These grooves, or striations are shown in FIG. 3 highly exaggerated for better illustration. The protective tube 38″ may be made of metal, or of ceramic material, and connected for example, as shown in FIG. 1 or FIG. 2, respectively. In FIG. 3 it is shown as made of metal, and hence the connection arrangement of FIG. 1 would be suitable. As before, the elements described in FIG. 3 correspond to those previously described in connection with FIGS. 1 and 2, and similar elements have been similarly numbered, but with a double prime notation.

The sensors 10, 10′ and 10″ are sturdy and can be easily and inexpensively made. By suitable choice of the diffusion resistance element, a wide variety of uses for sensors of this type can be provided, with mere change of the diffusion resistance portion 43/1, for example, or 43/2. A wide scope of requirements, as well as of response speed can be met, for example to monitor the composition of an atmosphere within a furnace, or burner space; control of combustion conditions with respect to drift in burner or furnace installations; warning sensors for lack of oxygen, in combustion sensors and the like.

The sensors of FIGS. 1, 2 and 3 can also be used in atmospheres which are contaminated and, for example, would result in contaminated deposits on the sensor. In such arrangements, it is desirable to place filter element, for example, a dust or particle-filter ahead of the diffusion resistance element 43/1, 43/2, respectively. Such filters are well known and any suitable filter construction may be used. Such a filter may be applied, suitably, directly ahead—with respect to penetration of sensing or test gas—of the diffusion resistance element 43/1, 43/2, respectively, secured, for example, to the protective tube 38,38′. Heat and combustion temperature resistant material, of course, should be used.

Various changes and modifications may be made in features described in connection with any one of the embodiments may be used with any of the others, within the scope of the inventive concept.

For example, a strip of insulating material 36a can be placed on the solid electrolyte body, and beneath the measuring electrode (15) to limit and control the extent of engagement of the measuring electrode with the solid electrolyte body, particularly in the region of the sealing-and-connecting element 36,40.

I claim:

1. A polarographic oxygen sensor, to measure the concentration of oxygen in gases, especially exhaust gases from a combustion process, having
   a metal housing (25);
   a closed solid electrolyte tubular body (12) sealingly secured to the housing;
   a reference electrode (18) located in the inside of the solid electrolyte body (12);
   a gas measuring electrode (15) located at the outside of the solid electrolyte body (12);
   means (5,25,31) applying a bias voltage, having a value in the range of about $\frac{1}{2}$ to $1\frac{1}{2}$ volts, across said electrodes (15,18), to cause a current to flow, the value of said current depending upon the reaction, with said measuring electrode (15), of the oxygen in the gas reacting said measuring electrode (15);
   means (7) providing a signal representative of the value of said current flow;
   a protective sleeve (38), essentially solid throughout its length except for an opening (41) formed therein, sealingly secured to the metal housing (25) and surrounding the tubular solid electrolyte body (12);
   wherein, to facilitate economical manufacturing,
   said protective sleeve (38) includes a diffusion resistance zone (43/1, 43/2), which can be constructed separately from said electrolyte body (12) and said electrodes (15,18), across said opening (41) which is gas-permeable for oxygen molecules and forms a diffusion resistance element, which sufficiently throttles migration of oxygen molecules to the measuring electrode (15) on the solid electrolyte body (12) to control the speed of the consequent reaction and hence, the value of the current which flows, and thereby assure that the sensor operates under diffusion-limited-current conditions,
   and wherein, to increase response speed of the sensor, the protective sleeve is tubular and surrounds the solid electrolyte body with a small but finite space (39″) therebetween defined by grooves, striations, or a roughened surface, sufficient to allow for vibration and to permit permeation of oxygen molecules, passing to the inside of the protective sleeve, through said diffusion resistance element (43/1, 43/2) and along at least a portion of the measuring electrode (15) on the surface of the solid electrolyte body (12).

2. Sensor according to claim 1, wherein the protective sleeve (38) loosely surrounds and engages the solid electrolyte body (12), leaving sufficient space to permit permeation of oxygen molecules along at least a portion of the measuring electrode without leaving so much space that oxyen passing through said diffusion resistance element mixes with other air in said space rather than reacting promptly with said measuring electrode and that the response speed of the sensor to changes in the oxygen level is slowed.

3. Sensor according to claim 1 wherein at least one of the surfaces of the measuring electrode (15), the solid electrolyte tubular body (12) and the gas tight protective sleeve (38), which are facing each other, is roughened, and the protective sleeve engages the solid electrolyte body and the measuring electrode (15) thereon, the surface roughness on at least one of the engaging surfaces permitting permeation of oxygen molecules along at least a portion of the measuring electrode (15).

4. Sensor according to claim 3 wherein the protective sleeve (38") engages, in part, the measuring electrode (15").

5. Sensor according to claim 3 wherein the protective sleeve is made of metal.

6. Sensor according to claim 3 wherein the protective sleeve is made of ceramic.

7. Sensor according to claim 3 wherein the protective sleeve (38) is formed with a bottom portion (42,42');

and wherein the diffusion resistance element (43/1,43/2) is located at the bottom portion (42,42') of the protective sleeve.

8. Sensor according to claim 3 wherein the protective sleeve (38) comprises a sealed tubular element (38) and a carrier (43) closing off the bottom (42) of the sleeve adjacent the closed end portion of the solid electrolyte body;

and wherein the diffusion resistance zone forming the diffusion resistance element (43/1) is located on said carrier element.

9. Sensor according to claim 8 wherein the carrier element (43) is sealed to the protective sleeve;

and wherein said carrier elements includes the diffusion resistance element.

10. Sensor according to claim 9 wherein the carrier element (43) comprises metal.

11. Sensor according to claim 9 wherein the carrier element comprises ceramic.

12. Sensor according to claim 3 wherein the diffusion resistance zone (43/1,43/2) comprises a region of the protective sleeve formed with at least one channel to thereby define said diffusion resistance element.

13. Sensor according to claim 3 wherein the diffusion resistance zone (43/1,43/2) comprises a region of the protective sleeve formed with gas-permeable pores to thereby define said diffusion resistance element.

14. Sensor according to claim 3 wherein said diffusion resistance element has openings therein of such a size that gas-phase diffusion therethrough is possible.

15. Sensor according to claim 3 wherein said diffusion resistance element has openings therein of such a size that Knudsen diffusion is possible.

16. Sensor according to claim 3 wherein a gas tight insulating layer (36a) is provided, secured to a first portion of a solid electrolyte body (12,12') remote from the closed end of the solid electrolyte tubular body, and interposed between the solid electrolye body and the measuring electrode (15,15').

17. Sensor according to claim 3 further comprising holding means (44,45,46), selectively separably retaining the protective sleeve (38') on the metal housing (25).

18. Sensor according to claim 3 further including a heater element (22) extending into the interior of the closed solid electrolyte tubular body (12).

19. A polarographic oxygen sensor according to claim 1, wherein said diffusion resistance element throttles oxygen diffusion to such an extent that migration conditions will occur which are comparable to measuring oxyten concentration in liquid in which the diffusion speed is reduced by a factor of about $10^5$.

* * * * *